United States Patent [19]

Abraham et al.

[11] Patent Number: 4,686,183

[45] Date of Patent: Aug. 11, 1987

[54] PROCESS FOR THE MANUFACTURE OF P-MENTH-8-ENE-1,2-DIOL

[75] Inventors: Wolf-Rainer Abraham, Braunschweig; Burkhard Stumpf, Königslutter; Klaus Kieslich, Braunschweig, all of Fed. Rep. of Germany

[73] Assignee: Gesellschaft für Biotechnologische Forschung mbH (GBF), Braunschweig-Stöckheim, Fed. Rep. of Germany

[21] Appl. No.: 542,654

[22] Filed: Oct. 17, 1983

[30] Foreign Application Priority Data

Oct. 26, 1982 [DE] Fed. Rep. of Germany ....... 3239545

[51] Int. Cl.[4] .......................... C12P 7/18; C12N 1/14; C12R 1/645
[52] U.S. Cl. .................................. 435/158; 435/254; 435/911
[58] Field of Search ....................... 435/158, 254, 911

[56] References Cited

PUBLICATIONS

Mokherjee, B. et al., *Applied Microbiology*, vol. 25, No. 3, pp. 447–453, 1973.
Bowen, E. R., *Proc Flastate Hortic Soc.*, vol. 88, pp. 304–308, 1976, Chem Abst 85:19027r, p. 504, 1976.
Prema, B. R. et al., *Applied Microbiology*, vol. 10, pp. 524–528, 1962, Chem Abst 10539b, 1962.
Ballal, et al., *Biochem & Biophys Res Comm*, vol. 23, (4), pp. 473–478, 1966.
Ballal et al, *Biochem & Biophys Res Comm*, vol. 29 (3), pp. 275–280, 1967.
Rosazza, J. P. (Ed), *Microbial Transformations of Bioactive Compounds*, vol. I, pp. 90–92, CRC Press Inc., 1982.
Prema et al., *Applied Microbiology*, vol. 10, pp. 529–531 (1962).
Dhavalikar et al., *Indian J. Biochem.*, vol. 3, pp. 144–157 (1966).

*Primary Examiner*—Thomas G. Wiseman
*Assistant Examiner*—Jayme A. Huleatt
*Attorney, Agent, or Firm*—Marmorek, Guttman & Rubenstein

[57] ABSTRACT

The invention relates to a process for the manufacture of p-menth-8-ene-1,2-diol by the microbiological conversion of limonene in the presence of various fungi.

2 Claims, No Drawings

PROCESS FOR THE MANUFACTURE OF P-MENTH-8-ENE-1,2-DIOL

Microbiological conversions of limonene have been known for a relatively long time[1]. The described reactions were, however, first of all the results of investigations into the decomposition of limonene, which had not been clearly described, with pseudomonades[2-8] and enterobacteriaceae[9,10]. The substrate was used as the carbon and energy source for these micro-organisms. *Aspergillus niger* NCIM 612 oxidises limonene to (+)-cis-carveol, alpha-terpineol and secondary products[11]. In the case of all of the metabolites, however, it was possible to isolate only small substance quantities as intermediate products of decomposition.

In contrast, a strain of *Corynebacterium hydrocarboclastus* cultured on hydrocarbon oxidises the co-substrate limonene to carvone which is obtained in a preparative yield[12].

Cis- and trans-p-menth-8-ene-1,2-diol have hitherto been described only without allocation to the 4(S)- or 4(R)-structure series as intermediate stages or bacterial limonene decomposition[9].

According to the invention, it has now been established that, in the case of biotransformations of (R)(+)-limonene, the defined (1S,2S,4R)-p-menth-8-ene-1,2-diol can be manufactured preparatively. Suitable for this conversion are various fungi of the genera Fusarium, such as *Fusarium oxysporum* DSM 62297; Gibberella, such as *Gibberella cyanea* DSM 62719 and *Gibberella heterochroma* DSM 62720; Chaetomium, such as *Chaetomium globosum* DSM 62109 and *Chaetomium cochliodes* DSM 1909; Diplodia, Such as *Diplodia oleae* CBS 17453 and *Diplodia gossypina* ATCC 10936; Corynespora, such as *Corynespora cassiicola* DSM 62474 and DSM 62475 and *Corynespora melonis* CBS 12925; Glomerella, such as *Glomerella miyabeana* DSM 62731, *Glomerella capsulata* DSM 1166 and *Glomerella cingulata* ATCC 12097; Aspergillus, such as *Aspergillus sclerotiorum* DSM 63357 and *Aspergillus caespitosus* CBS 10345; Pestalotia, such as *Pestalotia microspora* ATCC 11816; Streptomyces, such as *Streptomyces rimosus* NRRL 2234; Botryodiplodia, such as *Botryodiplodia theobromae* DSM 62078; Botryosphaeria, such as *Botryosphaeria berengeriana* ATCC 12577.

*Diplodia gossypina* ATCC 10936 and *Corynespora cassiicola* DSM 62474 and DSM 62475 are preferred, in some cases only small quantities of secondary products being formed.

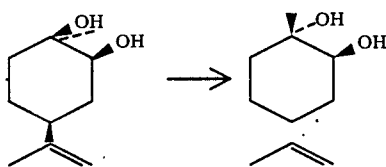

In a similar manner (S)(−)-limonene is converted by the same fungi in preparative yields to form the defined (1R,2R,4S)-p-menth-8-ene-1,2-diol.

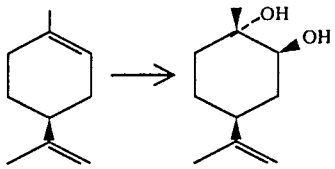

In a similar manner, but preferably with *Diplodia gossypina* and *Corynespora cassiicola*, racemic limonene, i.e. a mixture of (R)(+)-limonene and (S)(−)-limonene, is also converted to the corresponding mixture of (1S,2S,4R)-and (1R,2R,4S)-p-menth-8-ene-1,2-diol.

The fermentation conditions that must be used correspond to the prior art [1].

Apart from the species and strains specifically mentioned it is possible for the person skilled in the art as a matter of routine (especially using the colour reaction of p-menth-8-ene-1,2-diol described in Example (1) to ascertain other usable species and other usable strains.

The substances that can be manufactured according to these processes are starting materials for further chemical syntheses, which is demonstrated, for example, by dehydration to form the corresponding cis-mentha-2,8-dien-1-ols, which are starting structures for tetrahydrocannabinols[13].

EXAMPLE 1

For the pre-culture, a 100 ml Erlenmeyer flask with 20 ml of sterilised culture medium, containing 1% D(+)-glucose, 2% malt extract, 1% universal peptone (Merck) and 0.5% yeast extract, is first of all inoculated with 3 inoculation loops of a 7-day old sloping agar culture of *Corynespora cassiicola* DSM 62475 and incubated for 72 hours in the dark at 27° C. while agitating.

This culture is then transferred under aseptic conditions into a 2000 ml Erlenmeyer flask containing 400 ml of culture medium and cultivated for 48 hours under the conditions indicated above.

Since this organism has a tendency in a submerged culture not to grow homogeneously through the culture solution but rather to form "mycelium lumps" of various forms, the pr-culture is comminuted in the agitating flask using a sterilisable magnetic cutting device[14] and incubated for a further 24 hours.

Five 2000 ml fermenter flasks, each also containing 400 ml of culture medium, are each inoculated with 20 ml of this pre-culture and pre-fermentation is carried out for 64 hours. 85 mg of (R)(+)-limonene are then added to each flask. After 8 hours in each case, 85 mg of educt are added twice more and, after a total contact time of 48 hours, the fermentation is terminated after completion of the reaction.

The course of the conversion is followed by means of thin layer chromatography. For this purpose, 0.2 ml of ethyl acetate is added to 1 ml of a sample taken under sterile conditions and the whole is agitated for 2 minutes and centrifuged for 2 minutes. 0.01 ml of the supernatant liquid is applied to HPTLC pre-coated plates, silica gel Si 60 (Merck), and 5 cm are developed with dichloromethane/acetone (80+20).

The plates are then sprayed with the following reagent:
 0.6 ml of anisic aldehyde
 1.0 ml of sulphuric acid
 50.0 ml of acetic acid In order to make the spots visible, incubation is carried out for 2 minutes at 100° C.

For preparative working-up, the supernatant liquid and the mycelium are extracted with ethyl acetate and concentrated to 5 ml.

Chromatographic separation is carried out in a silica gel column, Si 60 (Merck) (2 cm×35 cm), which is equilibrated against dichloromethane and, after applying the sample, is developed with a gradient of from 5 to 10% acetone in dichloromethane. 1.27 g (80% of the theoretical yield) are obtained.

EXAMPLE 2

This Example differs from Example 1 only in that (S)(−)-limonene is now used instead of (R)(+)-limonene.

1.21 g (76% of the theoretical yield) are obtained.

EXAMPLE 3

This Example differs from Example 1 only in that dl-limonene (dipentene) is used instead of (R)(+)-limonene.

1.23 g (77% of the theoretical yield) are obtained.

LITERATURE (1) K. Kieslich
   Microbial Transformations of Non-Steroid Cyclic Compounds
   Georg Thieme, Stuttgart 1976
(2) R. S. Dhavalikar, P. N. Rangachari, P. K. Bhattacharyya
   Ind. J. Biochem. 3, 158 (1966)
(3) N. R. Ballal, P. K. Bhattacharyya, P. N. Rangachari
   Biochem. Biophys. Res. Comm. 29, 275 (1967)
(4) N. R. Ballal, P. K. Bhattacharyya, P. N. Rangachari
   Biochem. Biophys. Res. Comm. 23, 473 (1966)
(5) N. R. Ballal, P. K. Bhattacharyya, P. K. Rangachari
   Ind. J. Biochem. 5, 1 (1968)
(6) B. L. Hugund, P. K. Bhattacharyya, P. N. Rangachari
   Arch. Microbiol. 71, 258 (1970)
(7) B. L. Hugund, P. K. Bhattacharyya, P. N. Rangachari
   Ind. J. Biochem. 7, 80 (1970)
(8) J. R. Devi, P. K. Bhattacharyya
   Biochem. Biophys. 14, 359 (1977)
(9) R. S. Dhavalikar
   Ind. J. Biochem. 3, 144 (1966)
(10) S. G. Dhere, R. S. Dhavalikar
   Sci. Cult. 36, 292 (1970)
(11) G. K. Swamy, K. L. Dhanchandani, P. K. Bhattacharyya
   Abstr. Sympos. on Recent Advances in the Chemistry of Terpenoids (Nation. Inst. of Sciences of India, New Delhi) (1965), 10.
(12) Hasegawa Co.
   Jap. Pat. 7 238998 (1972)
(13) R. W. Rickards, W. P. Watson
   Aust. J. Chem. 33, 451 (1980)
(14) B. Stumpf, L. Heuer
   Gebrauchsmuster Application G 8216 356.1

What is claimed is:

1. Process for the manufacture of a mixture of trans- and cis-p-menth-8-ene-1,2-diol, comprising fermenting racemic limonene with a p-menth-8-ene-1,2-diol producing fungus selected from the group consisting of *Gibberella cyanea* DSM 62719, *Diplodia gossypina* ATCC 10936, and *Corynespora cassiicola* DSM 62474 and 62475, and obtaining a mixture of trans- and cis-p-menth-8-ene-1,2-diol.

2. Process for the manufacture of trans- or cis-p-menth-8ene-1,2-diol, comprising fermenting R(+)-limonene or (S)(−)-limonene with a p-menth-8-ene-1,2-diol producing fungus selected from group consisting of *Giberella cyanea* DSM 62719, *Diplodia gossypina* ATCC 10936, and *Corynespora cassiicola* DSM 62474 and 62475, and obtaining trans- or cis-p-menth-8-ene-1,2-diol.

* * * * *